(12) United States Patent
Benabid et al.

(10) Patent No.: US 7,894,912 B2
(45) Date of Patent: Feb. 22, 2011

(54) NON-RECTILINEAR LEAD AND A SYSTEM FOR DEEP ELECTRICAL NEUROSTIMULATION INCLUDING SUCH A LEAD

(75) Inventors: Alim-Louis Benabid, Meylan (FR); Fabien Sauter-Starace, Seyssinet-Pariset (FR); Patrice Caillat, Grenoble (FR); Stephan Chabardes, Saint Martin D'Uriage (FR)

(73) Assignee: Commissariat a l'Energie Atomique, Paris (FR)

( * ) Notice: Subject to any disclaimer, the term of this patent is extended or adjusted under 35 U.S.C. 154(b) by 78 days.

(21) Appl. No.: 12/071,664

(22) Filed: Feb. 25, 2008

(65) Prior Publication Data

US 2008/0255646 A1    Oct. 16, 2008

(30) Foreign Application Priority Data

Feb. 26, 2007   (FR) .................................... 07 01353

(51) Int. Cl.
*A61N 1/00* (2006.01)
(52) U.S. Cl. ..................................... 607/116
(58) Field of Classification Search ................. 600/378, 600/507, 374, 423, 545, 585; 606/108, 192, 606/33, 41, 92; 607/116, 117, 157, 149, 607/45, 46; 604/104
See application file for complete search history.

(56) References Cited

U.S. PATENT DOCUMENTS 5,749,883 A * 5/1998 Halpern ...................... 606/159
5,964,753 A * 10/1999 Edwards ...................... 606/33

(Continued)

FOREIGN PATENT DOCUMENTS

EP    1 062 973    12/2000

(Continued)

OTHER PUBLICATIONS

Benabid, Alim L. et al., "Long-term suppression of tremor by chronic stimulation of the ventral intermediate thalamic nucleus" (1991) *The Lancet* vol. 337, pp. 403-406.

(Continued)

*Primary Examiner*—George Manuel
*Assistant Examiner*—Robert N Wieland
(74) *Attorney, Agent, or Firm*—Clark & Brody (57) ABSTRACT

A lead for deep brain electrical stimulation, to be inserted into liquid cavities, such as ventricles, or cysternae or subarachnoidal spaces, the lead comprising: a tubular body of biocompatible material having a side wall defining a lumen, said tubular body being suitable for being inserted over at least a fraction of its length into the inside of a patient's body in order to reach a region for stimulation; electrodes disposed close to a distal end of the tubular body; and a rigid stylet for inserting removably into the lumen of said tubular body; the lead being wherein said tubular body has an equilibrium shape that is not rectilinear, being different from the shape of the stylet and presenting one and only one bend, and that is sufficiently flexible and elastic to follow the shape of said stylet by deforming reversibly when the stylet is inserted into the lumen. A deep electrical neurostimulation system comprising an electrical pulse generator and at least one such lead having its electrodes electrically connected to said generator.

32 Claims, 5 Drawing Sheets

U.S. PATENT DOCUMENTS

| | | |
|---|---|---|
| 6,512,958 B1 | 1/2003 | Swoyer et al. |
| 6,673,042 B1 * | 1/2004 | Samson et al. ............... 604/104 |
| 7,033,326 B1 | 4/2006 | Pianca et al. |
| 2003/0009095 A1 * | 1/2003 | Skarda ....................... 600/374 |
| 2005/0203599 A1 * | 9/2005 | Garabedian et al. ......... 607/116 |
| 2006/0041295 A1 | 2/2006 | Osypka |
| 2006/0178720 A1 * | 8/2006 | Dadd et al. .................. 607/137 |
| 2006/0195157 A1 * | 8/2006 | Lee et al. ...................... 607/46 |
| 2009/0124978 A1 * | 5/2009 | Abrams et al. ......... 604/164.01 |

FOREIGN PATENT DOCUMENTS

| | | |
|---|---|---|
| WO | 02/078575 | 10/2002 |

OTHER PUBLICATIONS

Benabid, Alim-Louis et al., "Therapeutic electrical stimulation of the central nervous system" (2005) *C.R. Biologies* vol. 328, pp. 177-186.

Mayberg, Helen S. et al., "Deep Brain Stimulation for treatment-Resistant Depression" (2005) *Neuron* vol. 45, pp. 651-660.

Medtronic Manual; DBS Lead Kit for Deep Brain Stimulation, (2005).

* cited by examiner

NON-RECTILINEAR LEAD AND A SYSTEM FOR DEEP ELECTRICAL NEUROSTIMULATION INCLUDING SUCH A LEAD

The invention relates to a lead for deep brain electrical stimulation, and also to a deep brain electrical stimulation system including at least one such lead.

BACKGROUND OF THE INVENTION

Deep brain electrical stimulation is a therapeutic technique comprising the implantation of a medical device known as a brain stimulator that serves to send electrical pulses to specific portions of the brain, by means of leads for electrical stimulation implanted in the appropriate neural structures. For example, stimulating the thalamic nuclei or the subthalamic nuclei can be useful in treating motor disorders such as tremor as caused in particular by Parkinson's disease (see the article by A-L. Benabid, P. Pollak, C. Gervason, D. Hoffmann, D-M. Gao, M. Hommel, J-E. Perret, and J. de Rougemont "Long-term suppression of tremor by chronic stimulation of the ventral intermediate thalamic nucleus", The Lancet, Vol. 337, No. 8738, Feb. 16, 1991, pp. 403-406). In addition, stimulation of the subgenual cingulate cortex is being used experimentally for treating particularly severe forms of clinical depression that are resistant to treatment (H. S. Mayberg et al. "Deep brain stimulation for treatment-resistant depression", Neuron, Vol. 45, pp. 651-660, Mar. 3, 2005). Stimulation is also being tested on the posterior hypothalamic nuclei for treating cluster headaches, on periaqueductal gray matter for attenuating pain, and on the ventromedial hypothalamus for treating certain kinds of obesity (A-L. Bernabid, B. Wallace, J. Mitofanis, C. Xia, B. Piallat, V. Fraix, A. Batir, P. Krack, P. Pollak, and F. Berger "Therapeutic electrical stimulation of the central nervous system", Comptes Rendus Biologies, Vol. 328, No. 2, February 2005, pp. 177-186).

Under all circumstances, deep brain electrical stimulation involves inserting a flexible lead into the skull of the patient under guidance of a rigid stylet until the tip of said lead reaches the region of the brain that is to be stimulated. Close to its tip, the lead has electrodes or contacts (generally four in number), that are connected by a subcutaneous cable to a pulse generator, itself implanted under the skin of the patient, like a conventional cardiac pacemaker. After the introduction of the lead and its fixation to the patient's skull, the stylet which made the lead rigid and rectilinear, is extracted from the lead after serving for introducing the lead, and the lead can remain in place for a duration that may be as long as several years.

A more detailed description of the procedure of implanting a lead for deep brain electrical stimulation is given by the document "Medtronic—DBS™ Lead Kit For Deep Brain Stimulation 3387 3389—Implant manual", from the supplier Medtronic Inc., which can be downloaded from the following Internet site: http://www.medtronic.com/physician/activa/downloadablefiles/197928_b_006.pdf.

By way of example, leads for deep brain electrical stimulation of conventional type are described in the above document from the supplier Medtronic, and also in U.S. Pat. No. 6,512,958.

The rectilinear shape of the lead is generally made necessary in order to ensure that insertion is as little traumatic as possible for the patient. Nevertheless, given the constraints that limit the insertion paths that can be selected for being followed by the lead without giving rise to unacceptable lesions in brain tissue, such a shape does not always make it easy to access regions that present therapeutic interest.

In addition, since a lead for deep brain electrical stimulation is implanted permanently for a duration of several years, there is a major risk of its tip becoming slightly displaced over time, thereby compromising its therapeutic effectiveness.

Document EP 1 062 973 describes a lead made of a flexible material and presenting a distal or head end of curved shape. The lead is inserted into the brain of a patient via a rigid cannula; while inside the cannula, said head end takes on the rectilinear shape of the cannula and returns to its curved configuration on coming out form the cannula at the end of the insertion operation. Such a lead is intended mainly for performing electrophysiological measurements prior implanting an electrical stimulation lead proper, with the curved shape of its head end enabling it to explore a plurality of brain zones without it being necessary to extract it and reinsert it several times over. However, it is less suitable for permanent implantation since it is difficult to extract the cannula alone from the patient's skull while leaving the lead in place. In addition, using an insertion cannula of outside diameter that is necessarily greater than that of the lead itself makes the implantation operation more traumatic.

OBJECTS AND SUMMARY OF THE INVENTION

An object of the invention is to remedy at least some of the drawbacks of the prior art as set out above.

This object is achieved by a lead for deep brain electrical stimulation, the lead comprising: a tubular body of biocompatible material having a side wall defining a lumen, said tubular body being suitable for being inserted over at least a fraction of its length into the inside of a patient's body in order to reach a region for stimulation; a plurality of electrodes disposed close to a "distal" end of the tubular body and capable of being brought into contact with said region for stimulation within the body of said patient; and a rigid stylet for inserting removably into the lumen of said tubular body; wherein said tubular body has an equilibrium shape that is not rectilinear, being different from the shape of the stylet, and presenting one and only one bend, and that is sufficiently flexible and elastic to follow the shape of said stylet by deforming reversibly when the stylet is inserted into the lumen.

Said stylet may be rectilinear in shape.

The bend that characterizes the lead of the invention makes it possible to reach regions for stimulation that would not be easily accessible using a lead of the type known in the prior art, inside cavities where the end of the lead can return to its initial shape without injuring tissue structures. The bend may be sharp or progressive, forming an angle of less than 90°, and preferably lying in the range 10° to 50°, and it may present a radius of curvature lying in the range 1 millimeter (mm) to 5 centimeters (cm), approximately.

In addition, said tubular body presents, close to its distal end, a region that, when at equilibrium, forms a balloon, and that is shaped in such a manner as to lengthen and take on a configuration that is substantially linear when said stylet is inserted into the lumen. In this way, the lead, while in its linear configuration, can be inserted in the inside of a cavity in the body of a patient, and then it can be blocked inside said cavity by extracting the stylet so as to enable the lead to return to its equilibrium balloon shape. Since the balloon is situated at the distal end of the lead, i.e. at its tip, the balloon also performs a safety function, preventing said tip from injuring the parenchyma of the brain.

Advantageously, electrodes may be provided at said balloon-shaped region in order to enable a more extensive region of the patient's brain to be stimulated.

In correspondence with the balloon-shaped region, the side wall may present thickness that is smaller than in the remainder of said tubular body. In a variant or in addition, in correspondence with said balloon-shaped region, said side wall may form non-touching quarters that are spaced apart by longitudinal slots capable of closing up as a result of the elongation caused by inserting said stylet into said lumen.

In a lead of the invention, said tubular body is closed in correspondence with its distal end.

The tubular body may be made of a material selected from silicones; siloxanes; polyurethanes; polyvinyl chlorides; benzocyclobutenes (BCBs); polyimides; and parylenes, or any other supple and biocompatible synthetic material.

The equilibrium length of the lead may lie in the range 15 cm to 40 cm.

Said tubular body may present a section that is substantially circular, having a diameter lying in the range 0.5 mm to 5 mm, and preferably in the range 0.5 mm to 2 mm. Under such circumstances, the tubular body of the lead is preferably made by molding.

In a variant, said tubular body may present a section that is substantially rectangular, with thickness lying in the range 10 μm to 200 μm and width lying in the range 50 μm to 3 mm. Under such circumstances, the tubular body of the lead is preferably made by depositing thin layers. The shape of the extremity of the lead might be adapted to the specific morphology of the neural structures to be stimulated.

A lead of the invention may comprise at least one electrically conductive element extending in the lumen or within the side wall of said tubular body and forming electrical contacts with said electrodes. Said or each conductive element may extend to a "proximal" end of said tubular body, opposite from its said distal end, and may include connection means for connection to an electrical pulse generator for deep electrical neurostimulation. Conversely, this lead, may be used to register electrical activities generated in the vicinity of the contact electrodes In another aspect, the invention provides a system for deep electrical neurostimulation, the system comprising: an electrical pulse generator for deep electrical neurostimulation; and at least one lead as described above, in which the electrodes are electrically connected to said electrical pulse generator.

The lead of the invention is particularly suitable for treating:

chronic depression or obsessive compulsive disorders by stimulating the nucleus accumbens or any other periventricular area;

pain, by stimulating the periaquaductal grey matter;

cluster headaches, by stimulating the posterior hypothalamic nuclei;

some feeding disorders by stimulating the ventromedian hypothalamus;

memory deficits by stimulation of the limbic structures close to the ventricle wall, such as mamillary bodies, the trigonal formation and the mamillo-thalamic bundles; or any other functional disorder, which would respond to stimulation of periventricular neural structures.

BRIEF DESCRIPTION OF THE DRAWINGS

Other characteristics, details, and advantages of the invention appear on reading the following description made with reference to the accompanying drawings given by way of example and showing, respectively.

MORE DETAILED DESCRIPTION

Figure 3:
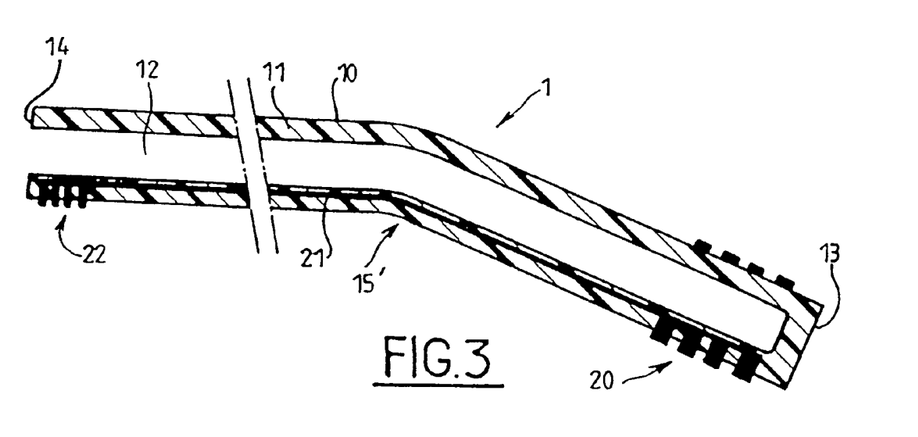
Figure 4:
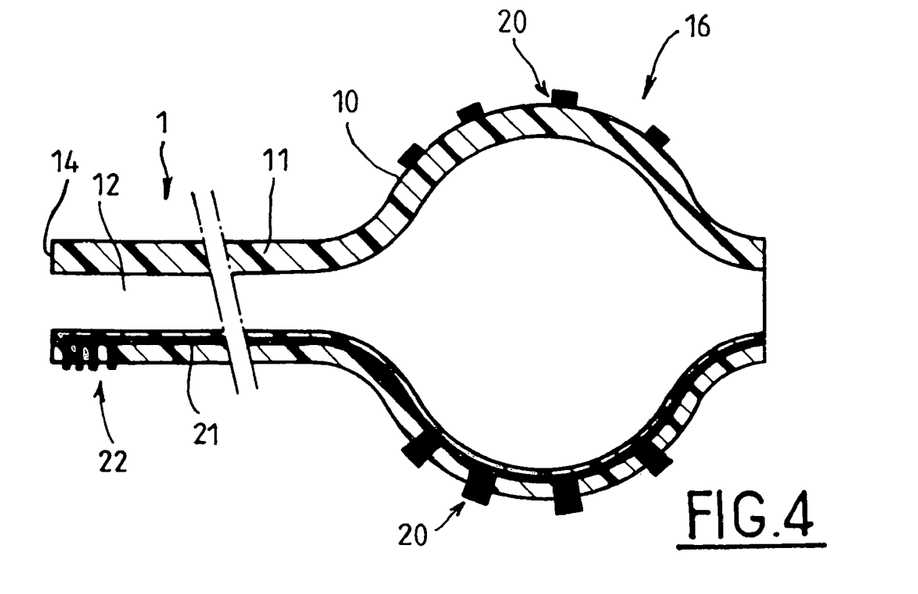
Figure 5:
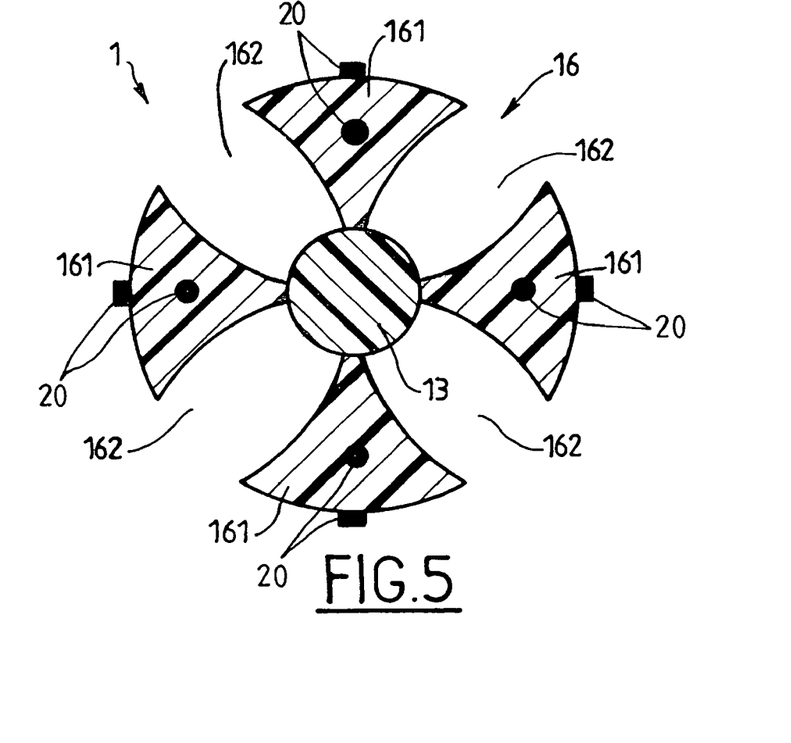
FIG. 5, an end view from the distal end of a lead constituting a fourth embodiment of the invention, likewise in its equilibrium configuration, without a stylet.

As shown in FIGS. 1 to 5, a lead 1 of the invention for deep electrical neural stimulation comprises a tubular body 10 having a side wall 11 that defines a lumen 12, and a rigid stylet 30 that can be inserted into said lumen 12. Insertion of the stylet 30 is made possible by the fact that a "proximal" end 14 of the tubular body 10 is open; the "distal" opposite end 13 is generally closed so as to prevent said stylet from escaping, and to allow exerting pressure to make the lead rectilinear. Electrodes 20, generally four in number, are placed close to said distal end 13 of the tubular body 10 and project from its side wall 11 so as to be capable of being brought into contact with a region of a patient's body for stimulation after the lead 1 has been inserted in said body. The electrodes 20 may be annular in shape, surrounding the tubular body 10, as can be seen in FIG. 5, but that is not essential and depends on the intended application. The electrodes 20 are connected to connection means 22 situated close to the proximal end 12 by means of conductor elements 21 such as wires or metal tracks, that extend within the lumen 12 of the tubular body 10, or within its side wall 11. The connection means 22 enable the lead 1 to be connected to an electrical pulse generator for neural stimulation of the brain (reference 40 in FIG. 14).

The length of the lead generally lies in the range 15 cm to 40 cm, with the exact value being a function of the specific application intended.

Figure 1:
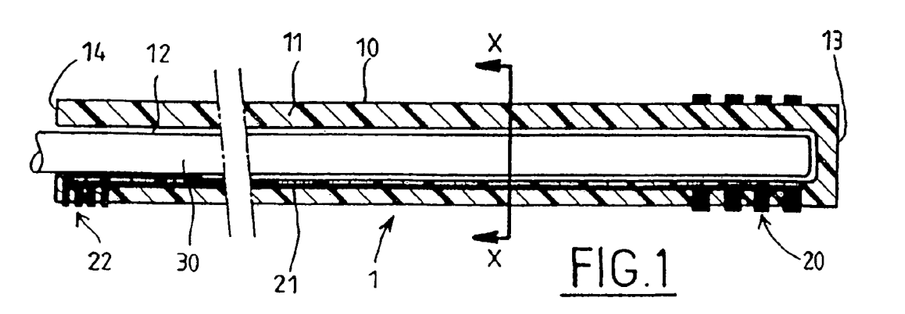
FIG. 1, a longitudinal section view of a lead of the invention in its insertion configuration, with a rigid rectilinear stylet inserted in the lumen of its tubular body.
Figure 2:
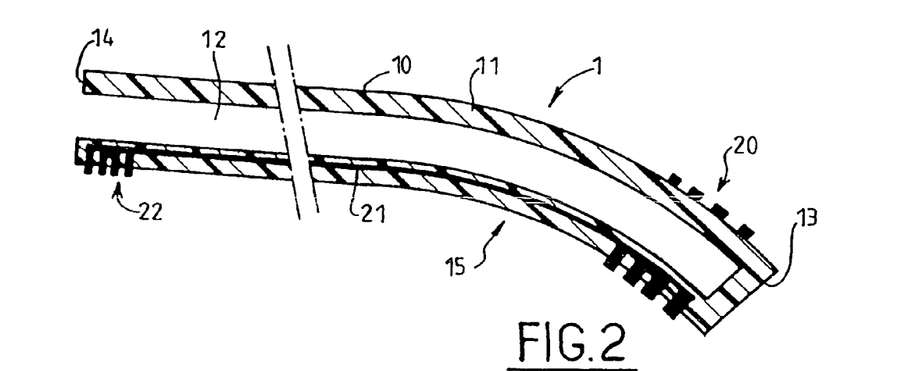
FIGS. 2, 3, 4, longitudinal section views of leads respectively in first, second, and third embodiments of the invention, each in its equilibrium configuration without a stylet.

As shown in FIGS. 2 to 4, the equilibrium shape of the tubular body 10 is not rectilinear. The term "equilibrium" shape is used to name the shape that the tubular body 10 takes when it is not subjected to any external force and when the stylet 30 is extracted from its internal lumen 12. For example, in a first embodiment shown in FIG. 2, the distal portion 15 of said tubular body 10 presents a progressive bend over a distance lying in the range 15 mm to 20 mm. In a second embodiment (FIG. 3), the tubular body 10 presents a sharp bend 15' situated close to its closed distal end 13, at about 10 mm therefrom.

The term "sharp" bend 15' is used to indicate that there is a sudden change in direction between two juxtaposed segments that are substantially rectilinear, whereas the term "progressive" bend 15 is used to mean that there is a rounded region producing a change of direction that is progressive. In general, the radius of curvature of the bend lies in the range 1 mm (sharp bend) to 5 cm (a bend that is very progressive).

In third and fourth embodiments (FIGS. 4 and 5), said tubular body 10 presents not only a bend 15 or 15', but also an enlargement defining a balloon-shaped region 16. This region presents a length of about 10 mm and is generally situated close to the distal end of the lead. The diameter of the balloon in the open configuration preferably lies in the range 2 mm to 8 mm. the diameter and the shape of the balloon (spherical, ovoid, or multiform), may vary, depending on the cavity in which the lead is inserted.

Whatever the embodiment under consideration, the material from which the tubular body 10 of the lead 1 is made needs to be sufficiently flexible and elastic to be able to follow the shape of the stylet 30 by deforming reversibly when the stylet is inserted into the lumen 12. Thus, inserting the stylet 30 causes the lead to straighten out. In the third or the fourth embodiment, the tip of the stylet 30 also comes to bear against the closed distal end 13 of the tubular body 10, thereby causing it to be lengthened; the lengthening preferably occurs in the balloon-shaped region 16 and in such a manner that the lead takes on a configuration that is substantially linear.

In the third embodiment (FIG. 4), the side wall 11 can be of reduced thickness in its balloon-shaped region 16, so as to ensure that the above-mentioned preferred lengthening occurs when the stylet 30 is inserted.

The fourth embodiment of the invention (FIG. 5) being wherein, in its balloon-shaped region 16, its side wall 11 is not continuous, but is made up of a plurality of non-touching quarters 161 that are spaced apart by longitudinal slots 162. When the stylet 30 is inserted in the lumen 12 and comes to bear against the distal end 13 of the lead, the traction force that acts on said side wall 11 tends to straighten out the quarters 161 and close the slots 162. The side wall may also present smaller thickness in the balloon-shaped region 16, but that is not essential, since the preferred lengthening is ensured by the presence of the slots 162.

The balloon 16 performs three functions. Firstly, it enables the lead to be blocked inside a ventricle of the brain. Secondly, it prevents the tip of the lead from penetrating into the parenchyma of the patient's brain and injuring it, as a result of some involuntary movement. Thirdly, electrodes 20 can be disposed on the balloon so as to make it possible to stimulate a region of the brain that is more extensive than when using the first or the second embodiment; in this case, the equilibrium shape of the balloon can be adapted to that of the cavity.

The use of a balloon of the type shown in FIGS. 4 and 5 can also be advantageous when using a rectilinear lead that does not present a bend.

Since it is designed to be inserted in the body of a patient, and more particularly in the patient's brain, the tubular body 10 needs to be made entirely, or at least so far as its outer portion is concerned, out of a material that is biocompatible. Biocompatible materials presenting properties of flexibility and elasticity that are sufficient for implementing the invention comprise, for example: silicones, siloxanes, polyurethanes, polyvinyl chlorides, benzocyclobutenes (BCBs), polyimides, and parylenes. The thickness of the side wall 11 of the tubular body 10 must also be selected in such a manner as to ensure the looked-for flexibility and elasticity, but also sufficient mechanical strength. For example, thickness lying in the range 100 µm to 1 mm can be appropriate for most applications.

The metal electrodes 20 must also be made out of biocompatible material, e.g. platinum iridium (Pt—Ir 90-10). Other conductor elements that are not designed to come into contact with the body of a patient but that are selected a priori to be biocompatible, may also be made out of graphite, of indium tin oxide (ITO), or out of alloys having a high elastic limit of the MP35N type, etc.

Figure 10:
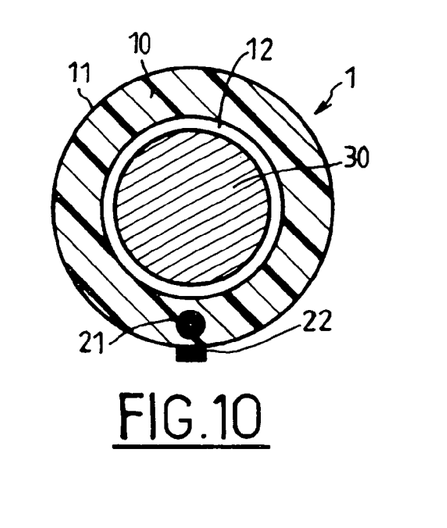
FIG. 10, a cross-section view on line X-X showing a lead of the invention, presenting a section that is substantially circular.
Figure 11:
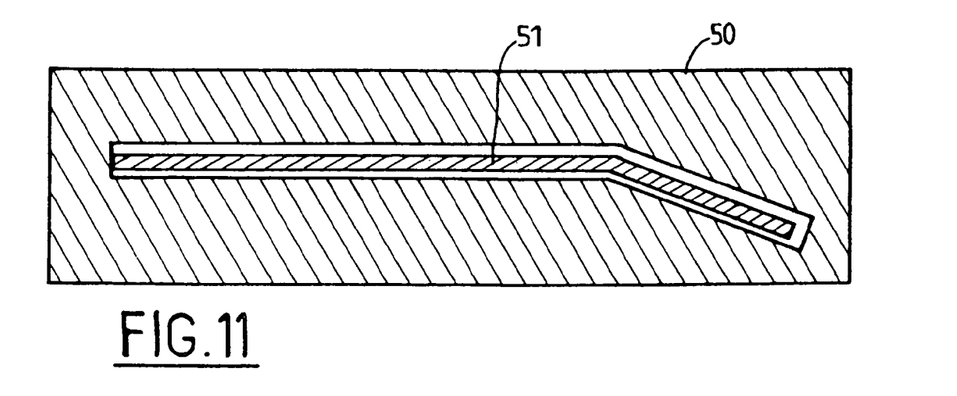
FIG. 11, a method of fabricating a lead constituting the first or second embodiment of the invention and presenting a section that is substantially circular.
Figure 12:
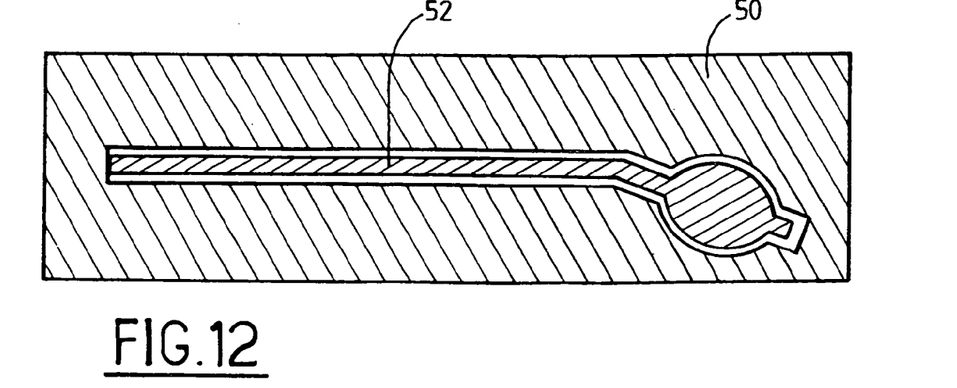
FIG. 12, a method of fabricating a lead constituting the third or fourth embodiment of the invention, and presenting a section that is substantially circular.

FIG. 10 is a cross-section through a lead 1 in which the tubular body 10 presents a section that is substantially circular, so it is generally cylindrical in shape, with a distal end 13 that is rounded (spherical). The diameter of the tubular body generally lies in the range 0.5 mm to 5 mm, and preferably in the range 0.5 mm to 2 mm, with the exact value depending on the specific application under consideration. A lead having a circular cross-section can be obtained by conventional injection molding techniques, as shown in FIGS. 11 and 12. An insert 51, 52 inserted into the mold 50 is used for making the internal lumen 12; the electrodes 20, the internal conductor elements 21, and the connection means 22 are also inserted into the mold 50 prior to injecting the plastics or elastomer material that constitute the side wall 11. For a lead of the balloon type, the insert 52 cannot be extracted simply from the tubular body 10 after it has been made. To solve this problem, it is possible to use an insert 52 made of wax or of paraffin, so that it can be extracted in the melted state, as in the lost wax casting process.

Molding methods also make it possible to provide leads of section that is not circular, but that is elliptical or polygonal, for example.

Figure 13:
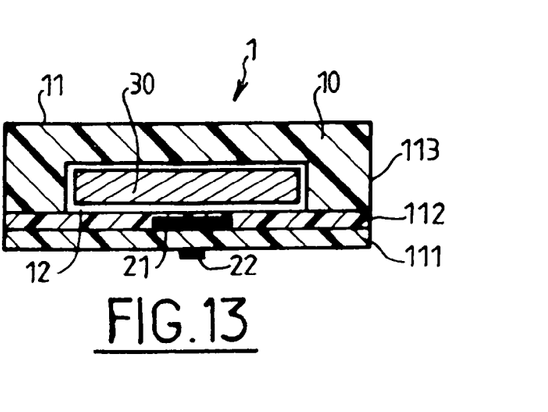
FIG. 13, a cross-section view on line X-X showing a lead of the invention, presenting a section that is substantially rectilinear.

In a variant, a lead of substantially rectangular shape as shown in FIG. 13 can be made by depositing thin layers by using methods such as centrifugal deposition, with the conductive layers (electrodes 20, internal conductors 21, connection means 22) being made using techniques borrowed from semiconductor or printed circuit technologies. The lumen 12 may be obtained using a sacrificial layer. A lead of this type may typically present a width lying in the range 50 µm to 3 mm and a thickness lying in the range 10 µm to 200 µm.

Figure 6:
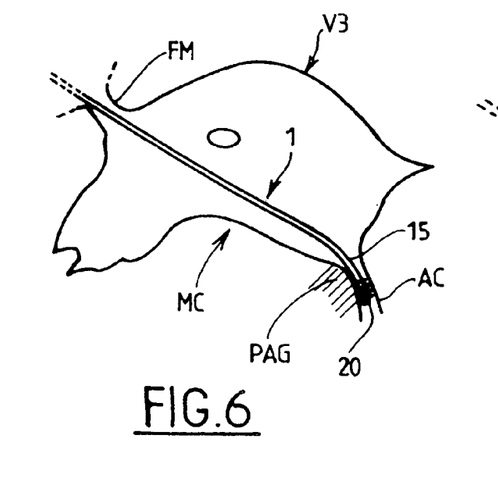
FIGS. 6, 7, 8, and 9, examples of lead applications in various embodiments of the invention.
Figure 7:
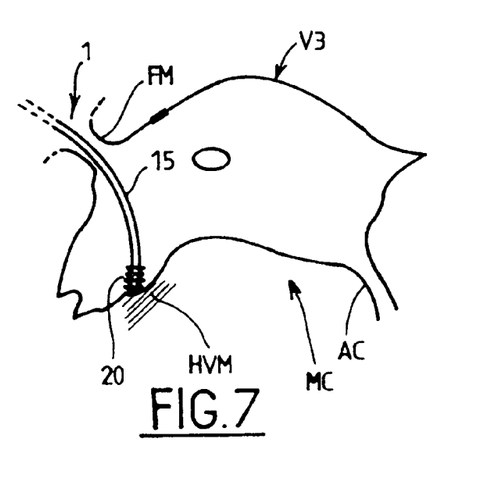
Figure 8:
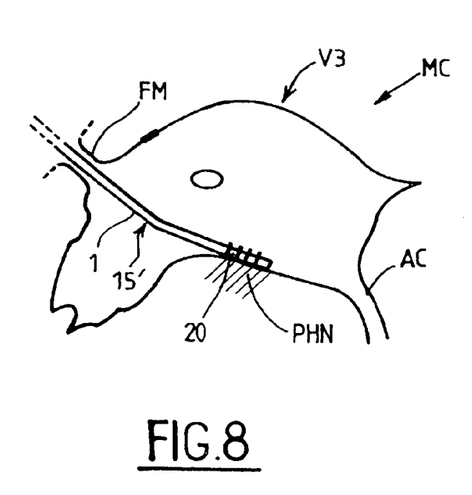

FIGS. 6 to 9 show examples of applications of leads constituted by various embodiments of the invention. In most circumstances, the lead is inserted into the third ventricle V3 of a human brain, that is filled with cerebrospinal liquid, and that opposes practically no resistance against the tubular body 10 returning to its equilibrium shape after the stylet 30 has been extracted. In the example of FIG. 6, a curved lead penetrates into the cerebral aqueduct AC to reach the periaqueductal gray matter PAG in order to treat pain. In the example of FIG. 7, a lead of the same type is used to reach the ventromedian hypothalamus HVM in order to treat certain feeding disorders responsible for obesity. In the example of FIG. 8, a bent lead stimulates the posterior hypothalamic nuclei in order to treat cluster headaches. In all these examples, the lead 1 is introduced into the third ventricle V3 by passing through the foramen of Monro FM in order to minimize the lesions caused to the cerebral cortex MC. It will be understood that using a conventional lead of rectilinear shape would not make it possible to reach these therapeutic targets while also following a path that is optimum from the point of view of collateral damage.

Figure 9:
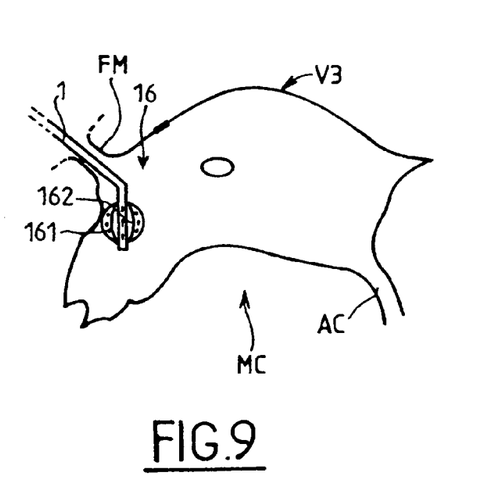

In the example of FIG. 9, a lead of the FIG. 5 type is inserted into the third ventricle and is blocked in this location by opening the balloon. Although this cannot be seen clearly in the figure, at least two quarters 161 of the balloon 16 come into contact with the parenchyma of the patient's brain: this produces better stimulation than with a "linear" lead.

Naturally, those are merely non-limiting examples of possible applications of the invention.

Under all of the circumstances considered above, it is assumed that the stylet 30 is rectilinear in shape. In reality, that does not constitute in any way an essential characteristic of the invention: on the contrary, the use of a stylet that is curved, but of a shape different from that of the tubular body 10 at equilibrium, can be advantageous for the purpose of minimizing the collateral damage caused by inserting the lead 1 into the patient's body, and help the progression of the lead into the cavity in order to be oriented.

Figure 14:
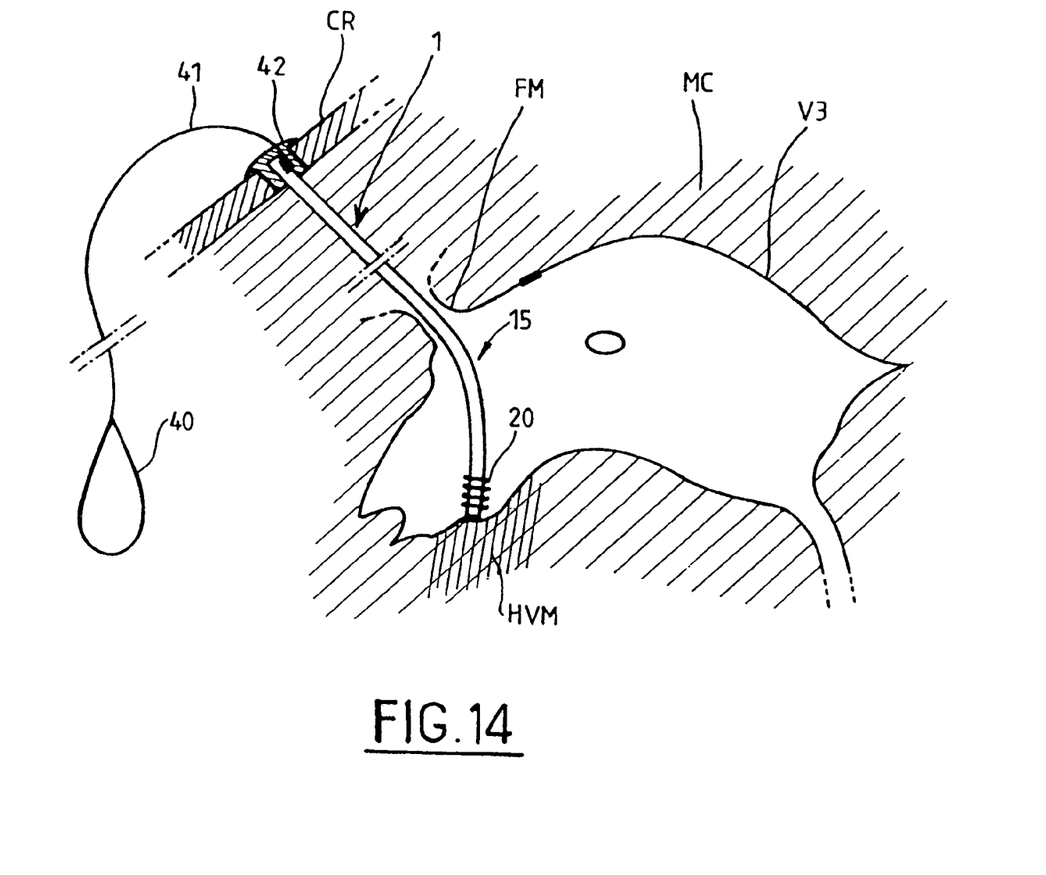
FIG. 14, a theoretical diagram of a deep brain electrical stimulation system comprising a lead constituting said first embodiment of the invention, inserted in the third ventricle of the brain of a patient.

FIG. 14 is a diagram showing a system for electrically stimulating the brain making use of a curved lead 1, shown in the deployed state inside the third ventricle V3 of a patient's brain, with its electrodes 20 in contact with the ventromedian hypothalamus HVM. In known manner, the tubular body 10 extends through the cerebral cortex MC and exits from the patient's skull via an orifice formed through the brain pan CR. At the level of this orifice, the tubular body is secured to the skull, according to the usual means used in this type of surgery (ligature, plug 42, clip, cement, etc.). In correspondence with the posterior end of the tubular body 10, the conductor elements 21 are connected via connection means 22 to a subcutaneous cable 41 that is in turn connected to an electrical pulse generator 40 for deep neurostimulation. The connection between the lead 1 and the subcutaneous cable 41 can be made using a connector placed under the epicranium (cranial periosteum) at distance of the skull orifice, where the electrodes come out.

What is claimed is:

1. A lead for deep brain electrical stimulation, the lead comprising:
   a tubular body of biocompatible material having a side wall defining a lumen, said tubular body being suitable for being inserted over at least a fraction of its length into the inside of a patients body in order to reach a region for stimulation;
   a plurality of electrodes carried by said tubular body and capable of being brought into contact with said region for stimulation within the body of said patient; and
   a rigid stylet for inserting removably into the lumen of said tubular body by a proximal end of said tubular body, which is opposed to a distal end of the tubular body;
   wherein said tubular body has an equilibrium shape that is not rectilinear, being different from the shape of the stylet, and presenting one and only one bend which separates the proximal and the distal end of said tubular body, which are not aligned with each other;
   said tubular body being made of a biocompatible material which is sufficiently flexible and elastic to straighten by following the shape of said stylet by deforming reversibly when the stylet is inserted into the lumen, and to recover its non-rectilinear equilibrium shape after extraction of said stylet; and
   said electrodes being carried by a distal part of the tubular body, close to said distal end.

2. A lead according to claim 1, in which said stylet is rectilinear in shape.

3. A lead according to claim 1, in which said bend is a progressive bend.

4. A lead according to claim 1, in which said bend is a sharp bend.

5. A lead according to claim 1, in which said bend forms an angle of less than 90°.

6. The lead according to claim 5, wherein the angle lies in the range 10° to 50°.

7. A lead according to claim 1, in which said bend presents a radius of curvature lying in the range 1 mm to 5 cm.

8. A lead according to claim 1, in which said tubular body is closed in correspondence with its distal end.

9. A lead according to claim 1, in which the said tubular body is made of a material selected from silicones; siloxanes; polyurethanes; polyvinyl chlorides; benzocyclobutenes; polyimides; and parylenes.

10. A lead according to claim 1, presenting a length at equilibrium lying in the range 15 cm to 40 cm.

11. A lead according to claim 1, in which said tubular body presents a section that is substantially circular, having a diameter lying in the range 0.5 mm to 5 mm.

12. The lead according to claim 11, wherein the diameter lies in the range 0.2 mm to 2 mm.

13. A lead according to claim 1, in which said tubular body presents a section that is substantially rectangular, with thickness lying in the range 10 µm to 200 µm and width lying in the range 50 µm to 3 mm.

14. A lead according to claim 1, including at least one electrically conductive element extending in the lumen or within the side wall of said tubular body and forming electrical contacts with said electrodes.

15. A lead according to claim 14, in which said or each conductive element extends to a "proximal" end of said tubular body, opposite from its said distal end, and includes connection means for connection to an electrical pulse generator for deep electrical neurostimulation.

16. A lead for deep brain electrical stimulation, the lead comprising:
    a tubular body of biocompatible material having a side wall defining a lumen, said tubular body being suitable for being inserted over at least a fraction of its length into the inside of a patient's body in order to reach a region for stimulation;
    a plurality of electrodes disposed close to a distal end of the tubular body and capable of being brought into contact with said region for stimulation within the body of said patient; and
    a rigid stylet for inserting removably into the lumen of said tubular body;
    wherein said tubular body has an equilibrium shape that is not rectilinear, being different from the shape of the stylet, and presenting one and only one bend, and that is sufficiently flexible and elastic to follow the shape of said stylet by deforming reversibly when the stylet is inserted into the lumen in which said tubular body presents, close to its distal end, a region that, when at equilibrium, forms a balloon, and that is shaped in such a manner as to lengthen and take on a configuration that is substantially linear when said stylet is inserted into the lumen.

17. A lead according to claim 16, in which electrodes are provided at said balloon-shaped region.

18. A lead according to claim 16, in which, in correspondence with said balloon-shaped region, said side wall presents thickness that is smaller than in the remainder of said tubular body.

19. A lead according to claim 16, in which, in correspondence with said balloon-shaped region, said side wall forms non-touching quarters that are spaced apart by longitudinal slots capable of closing up as a result of the elongation caused by inserting said stylet into said lumen.

20. A system for deep brain electrical stimulation, the system comprising:
    an electrical pulse generator for deep electrical neurostimulation; and
    at least one lead according to claim 1, in which the electrodes are electrically connected to said electrical pulse generator.

21. A method for electrostimulating a patient's brain, comprising:
    inserting in the patient brain a probe according to claim 1;
    directing the distal end of said probe into a cerebral cavity;
    retracting the stylet from said probe for allowing the tubular body thereof to recover its non-rectilinear equilibrium shape;
    contacting at least one of the electrodes of the probe with a periventricular region or a subarachnoidal area of the patient's brain; and
    applying a therapeutically effective electrical stimulation to said periventricular region or subarachnoidal area of the patient's brain through said at least one electrode.

22. A method according to claim 21, wherein said cerebral cavity is a third ventricle.

23. A method according to claim 22, wherein the periventricular region of the patient's brain is a nucleus accumbens.

24. A method according to claim 22, wherein the applied electrical stimulation is effective for treating chronical depression.

25. A method according to claim 22, wherein the applied electrical stimulation is effective for treating obsessive-compulsive disorder.

26. A method according to claim 22, wherein the periventricular region of the patient's brain is a periaquaductal grey matter, and wherein the applied electrical stimulation is effective for treating pain.

27. A method according to claim 22, wherein the periventricular region of the patient's brain is a posterior hypothalamic nucleus, and wherein the applied electrical stimulation is effective for treating cluster headaches.

28. A method according to claim 22, wherein the periventricular region of the patient's brain is a ventromedial hypothalamus, and wherein the applied electrical stimulation is effective for treating feeding disorders.

29. A method according to claim 22, wherein the periventricular region of the patient's brain is a limbic structure chosen between a mamillary body, a trigonal formation and a mamillo-thalamic bundle, and wherein the applied electrical stimulation is effective for treating memory deficits.

30. A method for electrostimulating a patient's brain, comprising:
    inserting in the patient brain a probe according to claim 17;
    directing the distal end of said probe into a cerebral cavity;
    retracting the stylet from said probe for allowing the tubular body thereof to recover its non-rectilinear equilibrium shape;
    contacting at least one of the electrodes of the probe with a periventricular region or a subarachnoidal area of the patient's brain; and
    applying a therapeutically effective electrical stimulation to said periventricular region or subarachnoidal area of the patient's brain through said at least one electrode.

31. A method according to claim 30, wherein the periventricular region of the patient's brain is chosen between a nucleus accumbens, a periaquaductal grey matter, a posterior hypothalamic nucleus, a ventromedial hypothalamus, a mamillary body and a trigonal formation.

32. A method according to claim 31, wherein the applied electrical stimulation is effective for treating a clinical condition chosen between chronic depression, an obsessive-compulsive disorder, pain, cluster headaches, a feeding disorder and memory deficits.

* * * * *